United States Patent
Cardosi et al.

(10) Patent No.: US 10,488,360 B2
(45) Date of Patent: Nov. 26, 2019

(54) METHOD OF USING AN ELECTROCHEMICAL DEVICE

(71) Applicant: INSIDE BIOMETRICS LIMITED, Dingwall (GB)

(72) Inventors: Marco Cardosi, Dingwall (GB); Stephen Blythe, Dingwall (GB)

(73) Assignee: INSIDE BIOMETRICS INTERNATIONAL LIMITED, Dingwall (GB)

(*) Notice: Subject to any disclaimer, the term of this patent is extended or adjusted under 35 U.S.C. 154(b) by 70 days.

(21) Appl. No.: 15/523,220

(22) PCT Filed: Oct. 29, 2015

(86) PCT No.: PCT/GB2015/053250
§ 371 (c)(1),
(2) Date: Apr. 28, 2017

(87) PCT Pub. No.: WO2016/067037
PCT Pub. Date: May 6, 2016

(65) Prior Publication Data
US 2017/0336339 A1    Nov. 23, 2017

(30) Foreign Application Priority Data
Oct. 31, 2014 (GB) .................................. 1419472.4

(51) Int. Cl.
*G01N 27/327* (2006.01)
*A61B 5/145* (2006.01)
(Continued)

(52) U.S. Cl.
CPC ....... *G01N 27/3274* (2013.01); *A61B 5/1451* (2013.01); *A61B 5/1477* (2013.01);
(Continued)

(58) Field of Classification Search
CPC ............ G01N 27/3274; G01N 27/301; G01N 33/48707; C12Q 1/006; C12Q 1/001;
(Continued)

(56) References Cited

U.S. PATENT DOCUMENTS

2007/0068806 A1    3/2007    Yang et al.
2011/0139635 A1    6/2011    Huang et al.
(Continued)

FOREIGN PATENT DOCUMENTS

EP    2292785 A1    3/2011
WO    WO-2005/045414 A1    5/2005
(Continued)

OTHER PUBLICATIONS

European Examination Report for corresponding European Patent Application Serial No. 15790221.4, dated Mar. 15, 2018, pp. 1-4.
(Continued)

*Primary Examiner* — J. Christopher Ball
(74) *Attorney, Agent, or Firm* — Tarolli, Sundheim, Covell & Tummino LLP (57) ABSTRACT

A method of using an electrochemical device includes at least first and second electrodes; a chamber for receiving a fluid sample and defining a volume partially bounded by a first portion of the first electrode and a second portion of the second electrode, the first portion having a first characteristic for influencing an electrochemical reaction at the first portion, the second portion having a second characteristic for influencing an electrochemical reaction at the second portion, the first and second characteristics having a predetermined relationship. The method also includes receiving a fluid sample in the chamber; measuring first and second electrical outputs at least one of the first and second elec-
(Continued)

trodes; and determining whether the first and second electrical outputs are related according to the predetermined relationship.

17 Claims, 10 Drawing Sheets

(51) Int. Cl.
*A61B 5/1477* (2006.01)
*A61B 5/157* (2006.01)
*A61B 10/00* (2006.01)
*C12Q 1/00* (2006.01)
*G01N 27/30* (2006.01)
*G01N 33/487* (2006.01)

(52) U.S. Cl.
CPC .......... *A61B 5/14517* (2013.01); *A61B 5/157* (2013.01); *A61B 10/007* (2013.01); *A61B 10/0051* (2013.01); *A61B 10/0064* (2013.01); *C12Q 1/001* (2013.01); *C12Q 1/006* (2013.01); *G01N 27/301* (2013.01); *G01N 33/48707* (2013.01); *A61B 2010/008* (2013.01); *A61B 2010/0067* (2013.01); *A61B 2010/0087* (2013.01); *A61B 2562/0295* (2013.01)

(58) Field of Classification Search
CPC ... A61B 5/14517; A61B 5/1477; A61B 5/157; A61B 5/1451; A61B 10/0051; A61B 10/0064; A61B 10/007
See application file for complete search history.

(56) References Cited

U.S. PATENT DOCUMENTS

| | | |
|---|---|---|
| 2011/0168575 A1 | 7/2011 | Lica et al. |
| 2012/0142117 A1 | 6/2012 | Ahn et al. |
| 2013/0277234 A1 | 10/2013 | Burke et al. |

FOREIGN PATENT DOCUMENTS

| | | |
|---|---|---|
| WO | WO-2005/078437 A1 | 8/2005 |
| WO | WO-2009/049015 A2 | 4/2009 |
| WO | WO-2010/095787 A1 | 8/2010 |
| WO | WO-2012/091728 A1 | 7/2012 |

OTHER PUBLICATIONS

International Search Report issued in PCT/GB2015/053250 dated Feb. 2, 2016.
Written Opinion issued in PCT/GB2015/053250 dated Feb. 2, 2016.
Hinkley, D.V., "On the Ratio of Two Correlated Normal Random Variables," *Biometrika*, vol. 56, No. 3, pp. 635-639 (1969).
Search Report issued in Great Britain Pat. Appl. No. 1419472.4 dated Apr. 30, 2015.

METHOD OF USING AN ELECTROCHEMICAL DEVICE

TECHNOLOGICAL FIELD

The present disclosure relates to a method of using an electrochemical device. In specific embodiments the disclosure relates to authenticating an electrochemical device such as an electrochemical test strip as used with bodily fluid monitors for determining the concentration of analytes in an individual's bodily fluid sample.

BACKGROUND OF THE DISCLOSURE

In the field of diagnostic devices such as used in the medical device industry, especially those used for analysing blood or other bodily fluid samples, it is often required for users to monitor biometrics such as the levels of certain chemicals, substances, or analytes present for example in their bloodstream. For instance, diabetics in particular must regularly monitor the concentrations of glucose in their blood in order to determine if they are in need of insulin. In order to respond effectively to an individual's needs to monitor blood sugar levels, diagnostic devices and kits have been developed over the years to allow an individual to autonomously determine the concentration of glucose in their bloodstream, in order to better anticipate the onset of hyperglycaemia or hypoglycaemia and take preventative action as necessary. The existence of such diagnostic devices places less strain on the healthcare system at large, as patients are able to administer insulin in their own home and without having to do so in the presence of a medical professional.

Typically, the patient will perform a fingerstick to extract a small drop of blood from a finger or alternative site, using a lancing device. An electrochemical test strip is then inserted into a diagnostic meter, and the sample is applied to the test strip. Through capillary action, the sample flows across a measurement chamber of the strip and into contact with one or more electrodes or similar conductive elements coated in sensing chemistry for interacting with a particular analyte or other specific chemical (for example glucose) in the blood sample. The magnitude of the reaction is dependent on the concentration of the analyte in the blood sample. The diagnostic meter may detect the current generated by the reaction of the reagent with the analyte, and the result can be displayed to the user.

It is important that a correct test strip is used by a user. For example, a strip is generally designed to detect the presence of one or more analytes, and a user must ensure that, when requiring a measurement of a particular analyte, a strip capable of detecting such an analyte is used, as otherwise an incorrect reading will be given. In addition, proper identification of a test strip can avoid the accidental or purposeful use of a damaged/counterfeit strip, which could be of a relatively lower quality and potentially dangerous to the user.

US 2011/0139635 A1, US 2007/0068806 A1 and WO 2009/049015 A2 are examples of prior art strip identification methods wherein for example resistance measurements at a pair of electrodes are compared to the areas of the electrodes. Alternatively, electrodes may be formed of different materials, and the meter may be arranged to measure the impedance of the electrodes to identify a strip inserted in the meter.

There nonetheless remains a need in the art for new and improved methods of identifying electrochemical devices and electrochemical test strips in particular, to avoid the potential drawbacks identified above. The presently described embodiments seek to address this need.

SUMMARY OF THE DISCLOSURE

In a first aspect, there is provided a method of using an electrochemical device. The electrochemical device comprises at least first and second electrodes, and a chamber for receiving a fluid sample and defining a volume partially bounded by a first portion of the first electrode and a second portion of the second electrode. The first portion has a first characteristic for influencing an electrochemical reaction at the first portion, and the second portion has a second characteristic for influencing an electrochemical reaction at the second portion. The first and second characteristics have a predetermined relationship. The method comprises receiving a fluid sample in the chamber; measuring first and second electrical outputs at at least one of the first and second electrodes; and determining whether the first and second electrical outputs are related according to the predetermined relationship.

One of the first and second electrodes may be a working electrode (e.g. an electrode at which an electrochemical reaction occurs). The other of the first and second electrodes may be a counter electrode, a reference electrode, or may perform the dual function of both a reference and a counter electrode (referred to herein as a counter/reference electrode). Of course, the electrochemical device may include more than two electrodes.

The fluid sample may be arranged to electrochemically react with the first and second portions. The first and second portions of the first and second electrodes may form a limit or boundary of the volume such that the first and second portions may be exposed to the interior of the chamber. When a fluid sample is applied to the test device, the fluid sample will therefore flow into contact with the first and second portions. The volume defined by the chamber may be bounded by other portions of the electrochemical device, for example insulating portions, dielectrics and/or a spacer as is typically used with electrochemical test strips.

The first and second characteristics may comprise various different properties of the first and second portions that are capable of influencing or affecting an electrochemical reaction at the first and second electrodes. As described below in more detail, the characteristics may include a surface area of the first and second portions, i.e. an area of the first and second electrodes that is within the chamber or otherwise capable of coming into contact with a fluid sample received in the chamber. The characteristics may comprise other properties such as a type of a sensing chemistry coating the first and/or second portions, a concentration of the sensing chemistry, an amount of sensing chemistry, or any other characteristic which if modified would affect an electrochemical reaction at the electrode.

The predetermined relationship may include any quantifiable relationship relating the first characteristic to the second characteristic. For example, the predetermined relationship may be a ratio of the first characteristic to the second characteristic.

Electrochemically reacting with the first and/or second portion may comprise an oxidation or reduction at the first and/or second portion. This may be in connection with a sensing chemistry applied to the first and/or second portion, or on the basis of the particular material used to form the first/second electrode. For example, in some embodiments sensing chemistry may only coat one of the first and second portions, for example if the non-coated portion comprises a Ag/AgCl electrode (for instance a Ag/AgCl reference electrode), which may react with the fluid sample.

The electrical outputs may be any measurable electrical characteristic measured or detected at either or both of the electrodes. For example, the electrical characteristic may include voltage, current, impedance, resistance, capacitance, etc. The first and second outputs may be measured at different times and under different conditions.

Determining whether the first and second electrical outputs are related according to the predetermined relationship may comprise determining a ratio of the first and second electrical outputs and comparing the ratio to a ratio of the first and second characteristics.

An advantage of the inventive method over prior art methods is that no additional features or technologies are required to be incorporated onto the test device to achieve the identification step. This reduces the complexity, cost and number of manufacturing steps in producing the test device. Furthermore, as no additional features are required, the design on the test device is simpler, less crowded and therefore reduces print definition requirements and associated quality issues that may arise as a result of increased complexity.

In addition, by providing first and second portions within the chamber, the first and second portions having different characteristics capable of influencing an electrochemical reaction, the electrochemical device may provide an improved means of quality checking. For example, ferricyanide mediator has a tendency to be reduced in the presence of ambient light and moisture resulting in a gradual change of background current. If such an electrochemical test strip has been unintentionally modified or damaged in some manner (e.g. exposed to atmosphere for an extended period of time prior to use), the above-mentioned chemical change of the ferricyanide mediator will affect the predetermined relationship of the characteristics. This effect may be detected by a meter when reading the electrochemical test strip, and may cause the meter to reject the electrochemical device.

At least one of the first and second portions may comprise a sensing chemistry for electrochemically reacting with a fluid sample. The sensing chemistry may include a particular material (for example Ag/AgCl) used to form the electrode and arranged to react with the fluid sample. The sensing chemistries may be different, and for example may comprise different respective quantities of mediator and/or reagent. A quantity of the first sensing chemistry may be arranged to produce a first electrochemical response with a fluid sample, whilst a quantity of the second sensing chemistry may be arranged to produce a second electrochemical response with the fluid sample. The first and second electrochemical responses (which may be the first and second characteristics) may be related according to the predetermined relationship.

At least one of the first and second portions may be coated, partially or fully, with a sensing chemistry for electrochemically reacting with a fluid sample. Partially coating the first/second portion may alter the electrochemically active area of the first/second portion, and may therefore affect the characteristic of the portion.

The sensing chemistry may comprise at least one of a mediator and a reagent. The reagent may comprise non-active components (e.g. polymers, silica, etc.) that may affect the characteristic of the first/second portion, i.e. the characteristic capable of influencing an electrochemical reaction at the first/second portion. The reagent may also comprise active components also capable of influencing an electrochemical reaction at the first/second portion, such as enzymes, co-enzymes, and other electroactive components.

The first characteristic may comprise a first area of the first portion of the first electrode, and the second characteristic may comprise a second area of the second portion of the second electrode. The first and second areas may be the same or different. In some embodiments, the physical width of the electrode may be greater than that of the other electrode, resulting the first and second portions having different areas. In other embodiments, whilst the widths of the electrodes may be the same, the geometry or structure of the chamber may be altered so as to alter the areas of the first and second portions within the chamber, or otherwise bounding the volume defined by the chamber.

The predetermined relationship may comprise a ratio of the first area to the second area. At least one of the first area and the second area may comprise an area coated with a sensing chemistry. Thus, the electrochemically active area of the first and second portion may be varied by varying the surface area of the sensing chemistry coating.

The first characteristic may be a quantity of sensing chemistry comprised in the first portion, and the second characteristic may be a quantity of sensing chemistry comprised in the second portion. Thus, the first and second characteristics may depend on a quantity or concentration of sensing chemistry. The quantity or concentration of sensing chemistry at issue may be a particular component or chemical species of the sensing chemistry, for example one arranged to affect an electrochemically reaction with the fluid sample. The predetermined relationship may comprise a ratio of the quantity of the first sensing chemistry to the quantity of the second sensing chemistry.

The first characteristic may be a first concentration of a sensing chemistry coating the first portion, and the second characteristic may be a second concentration of a sensing chemistry coating the second portion. The first and second concentrations may be different or may be the same, e.g. may have a 1:1 ratio. The concentration may be a concentration of a particular chemical species within the sensing chemistry, such as an electrochemically active or non-active component of the sensing chemistry designed to electrochemically react with the fluid sample. In the case of sensing chemistry coating one of the first and second electrodes, and the other electrode comprising a Ag/AgCl electrode, the concentration may comprise a concentration of AgCl in the Ag/AgCl electrode. A concentration may also be a function of a thickness or volume of a layer or coating of sensing chemistry applied to one of the electrodes.

At least one of the first and second concentrations may comprise a surface area density or a volume density. The predetermined relationship may comprise a ratio of the first concentration to the second concentration.

Measuring the first and second electrical outputs may comprise applying a first potential difference across the first electrode and the second electrode; measuring the first electrical output; applying a second potential difference across the first electrode and the second electrode; and measuring the second electrical output. The second potential difference may be a reverse of the first potential difference, and may be greater or lesser in magnitude than the first potential difference. A relationship between the first and second potential differences may be predetermined.

The first and second electrical outputs may comprise respective first and second currents generated through the first electrode and the second electrode.

The electrochemical device may be an electrochemical test strip or a wearable electrochemical device. Electrochemical test strips may be any relatively small strip of material on which an electrochemical reaction is designed to take place. Typically the strips are small enough to be inserted into and read by a handheld diagnostic meter.

The method may further comprise authenticating the electrochemical device if the first and second electrical outputs are related according to the predetermined relationship. For example, authentication may occur if a ratio of the first and second characteristics is similar or identical to a ratio of the first and second electrical outputs. Once an electrochemical device is authenticated, the measured electrical outputs may be used for example by a diagnostic meter to determine a concentration of one or more analytes within the fluid sample.

The fluid sample may comprise a bodily fluid selected from the following: blood, plasma, urine, saliva, lacrimal fluid, sweat, and interstitial fluid; or breath condensate.

In accordance with a second aspect, there is provided a meter for reading electrochemical devices. The meter comprises means for receiving an electrochemical device. The electrochemical device comprises at least first and second electrodes, and a chamber for receiving a fluid sample and defining a volume partially bounded by a first portion of the first electrode and a second portion of the second electrode. The first portion has a first characteristic for influencing an electrochemical reaction at the first portion, and the second portion has a second characteristic for influencing an electrochemical reaction at the second portion. The first and second characteristics have a predetermined relationship. The meter further comprises means for receiving a fluid sample in the chamber. The meter further comprises means for measuring first and second electrical outputs at at least one of the first electrode and the second electrode, when an electrochemical device is received in the meter and when a fluid sample is received in the chamber. The meter further comprises one or more processors configured to determine whether the first and second electrical outputs are related according to the predetermined relationship.

The one or more processors may be further configured to authenticate the electrochemical device if the first and second electrical outputs are related according to the predetermined relationship.

In accordance with a third aspect, there is provided an electrochemical device comprising at least first and second electrodes, and a chamber for receiving a fluid sample and defining a volume partially bounded by a first portion of the first electrode and a second portion of the second electrode. The first and second portions are for influencing an electrochemical reaction. The first portion has a first area and the second portion has a second area different from the first area.

In accordance with a fourth aspect, there is provided an electrochemical device comprising at least first and second electrodes, and a chamber for receiving a fluid sample and defining a volume partially bounded by a first portion of the first electrode and a second portion of the second electrode. The first portion comprises a first sensing chemistry arranged to electrochemically react with a fluid sample. The second portion comprises a second sensing chemistry arranged to electrochemically react with the fluid sample. A quantity or concentration of the first sensing chemistry is different to a quantity or concentration of the second sensing chemistry.

BRIEF DESCRIPTION OF THE DRAWINGS

Specific embodiments will now be described in conjunction with the accompanying drawings, of which.

DETAILED DESCRIPTION

The present disclosure seeks to provide an improved method of identifying, validating or authenticating an electrochemical device. Whilst various embodiments are described below, the contemplated embodiments are not limited to those described herein, and variations of these embodiments may well fall within the scope of the appended claims.

Figure 1:
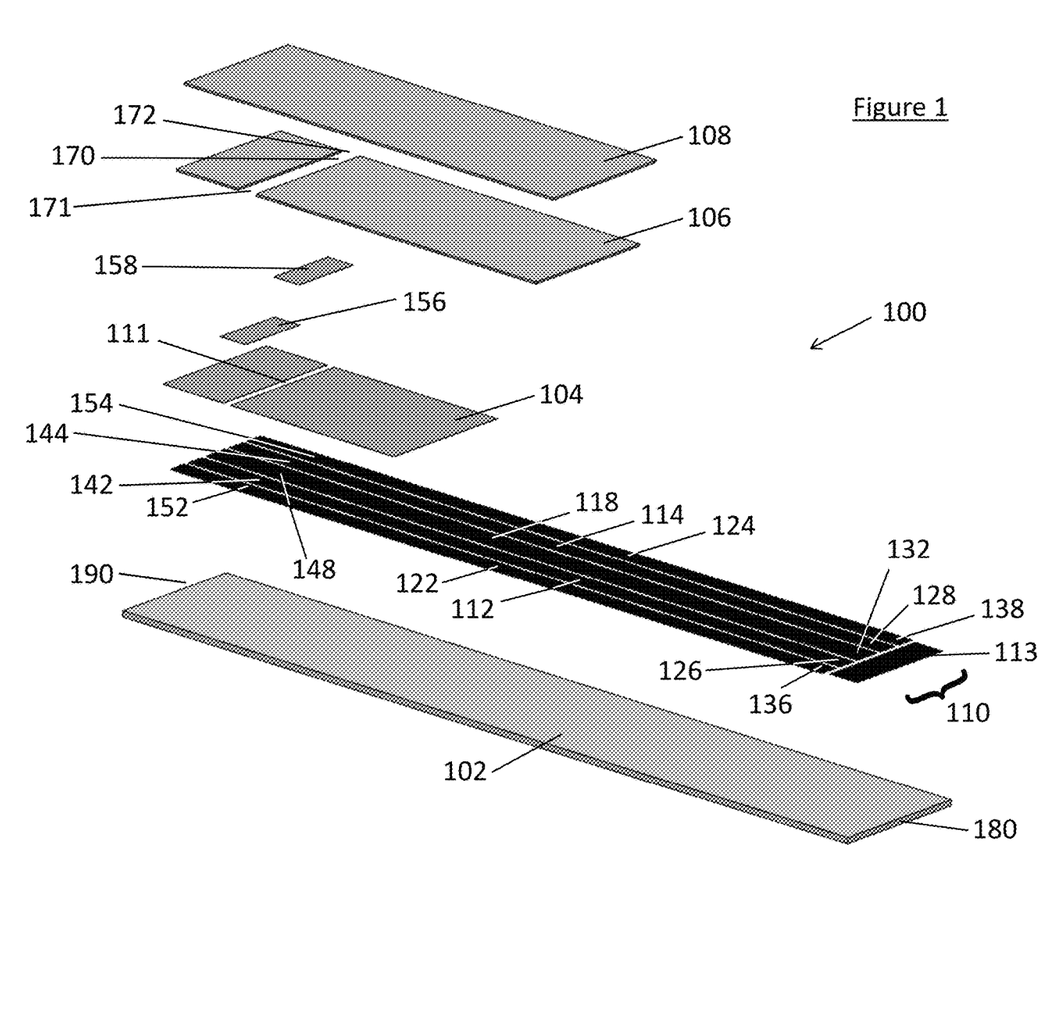
FIG. 1 is an exploded view of an embodiment of an electrochemical test strip that may be used with the described embodiments.

An electrochemical test strip, test strip or simply strip, as may be used with the described embodiments is shown in exploded form in FIG. 1. Test strip 100 is an 8 mm-wide strip and includes a number of so-called coplanar electrodes in that the electrodes are adjacent one another and share a common plane. This is in contrast to test strips having co-facial electrodes, whereby the electrodes are parallel yet in different planes, and effectively face each other. Whilst described in terms of its use with test strips having co-planar electrodes, embodiments may also be used with test strips having co-facing, or opposing, electrodes. Of course, strip 100 may take various other dimensions as required. A greater or lesser number of electrodes may be included on strip 100.

Test strip 100 is a multi-layered strip having a proximal end 180 and a distal end 190. Strip 100 comprises from bottom to top: first substrate layer 102, electrically conductive layer 110, dielectric insulation layer 104, reagent layers 156 and 158, patterned spacer layer 106, and second substrate layer 108.

First substrate layer 102 is typically formed of an inert polymeric material such as PET, polyethylene, polypropylene, PBT, ABS or polybutylene. Electrically conductive layer 110 is formed on top of first substrate layer 102 using screen-printing, thin-film evaporation followed by laser ablation, sputtering over a pre-formed mask, or electrolysis deposition. Other means of forming conductive layer 110 may be used, such as photolithography, although thick-film screen printing is preferred.

Conductive layer 110 comprises a plurality of electric tracks that connect the electrodes at distal end 190 of strip 100 to corresponding conductive pads at proximal end 180 of strip 100. The tracks run parallel to each other and substantially along the length of first substrate layer 102. In sequential order, conductive layer 110 comprises: first fill detect track 122, first working track 112, counter/reference track 118, second working track 114 and second fill detect track 124. Suitable materials for electrically conductive layer 110 include gold, carbon, graphene, platinum, palladium, gold/palladium composites, indium tin oxide film, platinised carbon and other typically low-resistance non-corroding materials as known to those skilled in the art.

At proximal end 180 of strip 100 each track defines a plurality of respective contact pads. In sequential order, conductive layer 110 comprises at distal end 180: first fill detect contact pad 136, first working contact pad 126, counter/reference contact pad 132, second working contact pad 128 and second fill detect contact pad 138. Pads are arranged to make electrical connection with corresponding circuit components of a strip meter or reader when strip 100 is inserted into the meter. A meter switch-on bar 113 is included adjacent the contact pads, although in other embodiments activation of the meter may be carried out using other means, for example across an end of one of the tracks.

At distal end 190 of strip 100, the tracks define co-planar electrodes arranged side-by-side and in parallel to one another. In sequential order, the electrodes comprise: first fill detect electrode 152, first working electrode 142, counter/reference electrode 148, second working electrode 144 and second fill detect electrode 154.

The electrodes are covered by insulation layer 104 having an open area or spacing 111 allowing a portion of each of the electrodes to remain uncovered. First and second reagent layers 156 and 158 (containing for example an enzyme, mediator, buffer salts, polymers, viscosity modifiers, etc.) are then deposited on insulation layer 104, and in particular over spacing 111, so as to bring reagent layer 156 into contact with fill detect electrode 152, first working electrode 142 and counter/reference electrode 148, and so as to bring reagent layer 158 into contact with counter/reference electrode 148, second working electrode 144, and second fill detect electrode 154.

A chamber-defining spacer layer 106 is then laid on top of insulation layer 104 so as to cover insulation layer 104. Spacer layer 106 defines sample-receiving chamber 170 which is positioned over first and second reagent layer 156 and 158. Chamber 170 is bounded at both ends by apertures 171 and 172, and defines a volume at least partially restricted or bounded by portions of reagent layers 156 and 158. Spacer layer 106 includes an adhesive layer on its underside so as to allow spacer layer 106 to adhere to the tracks and electrodes of conductive layer 110 as well as to insulation layer 104.

Second substrate layer 108 which is a transparent layer is then positioned over spacer layer 106, and adheres to spacer layer 106 using an adhesive layer on its underside after hydrophilic treatment to assist rapid and consistent sample filling. Second substrate layer 106 can be laid down individually or more preferably as a single pre-laminated layer, laminated to spacer layer 106.

Once test strip 100 is manufactured, a fluid sample such as a blood sample may be applied to test strip 100. Test strip 100 is a side-fill strip in that the fluid sample may be introduced from either side of strip 100 via either aperture 171 or aperture 172. However, it should be noted that embodiments may be used with end-fill strips, that is strips having a chamber arranged such that the sample may only be introduced into the chamber via a single entry point.

To apply the blood sample, a small volume (of the order of less than 1 mL and preferably of approximately 500 μL or less) is applied at an end of sample-receiving chamber 170, either via aperture 171 or aperture 172. Through capillary action, the sample will flow from one end of chamber 170 to the other end. The aperture through which the sample was not applied acts as an air vent as the blood flows from one aperture to the other.

The sample flows into contact with reagent layers 156 and 158 coating first and second working electrodes 142 and 148, counter/reference electrode 148, and first and second fill detect electrodes 152 and 154. For example, if the sample is introduced into chamber 170 via aperture 172 then the sample flows first into contact with reagent layer 158 coating second fill detect electrode 154, second working electrode 144 and counter/reference electrode 148. The sample will then flow into contact with reagent layer 156 coating counter/reference electrode 148, first working electrode 142 and first fill detect electrode 152.

As known in the art, specific analytes and other chemicals in the blood will react with reagent layers 156 and 158, depending on the reagent that is used. The reaction leads to an electrical current generated at the electrode and dependent on the concentration of the analyte in the blood. When strip 100 is inserted into a strip meter or other diagnostic meter, the current may be detected and converted into a signal for processing and display to a user. For example, if the meter is a glucose meter arranged to determine concentrations of glucose, the level of glucose in the blood applied to strip 100 may be inferred from the reaction that takes place.

In accordance with the presently described embodiments, reagent layer 156 coats a portion of working electrode 142 and a portion of counter/reference electrode 148, whilst reagent layer 158 coats substantially equal portions of counter/reference electrode 148 and working electrode 144. In the present embodiment, reagent layers 156 and 158 are non-overlapping though in other embodiments reagent layers 156 and 158 may overlap. Reagent layer 156 has a different concentration than reagent layer 158. For example, the concentrations of reagent in reagent layers 156 and 158 may be in a ratio of 1:2. Therefore, a different amount of reagent from reagent layer 156 coats working electrode 142 and counter/reference electrode 148, as compared to the amount of reagent of reagent layer 158 that coats counter/reference electrode 148 and working electrode 144. The different concentrations of reagent in reagent layers 156 and 158 represent different characteristics of reagent layers 156 and 158.

In related embodiments, whilst the concentrations of reagent in reagent layers 156 and 158 are different, the areas of working electrodes 142, 144 and counter/reference electrode 148 that are coated by reagent layers 156 and 158 may also be different.

Figure 2:
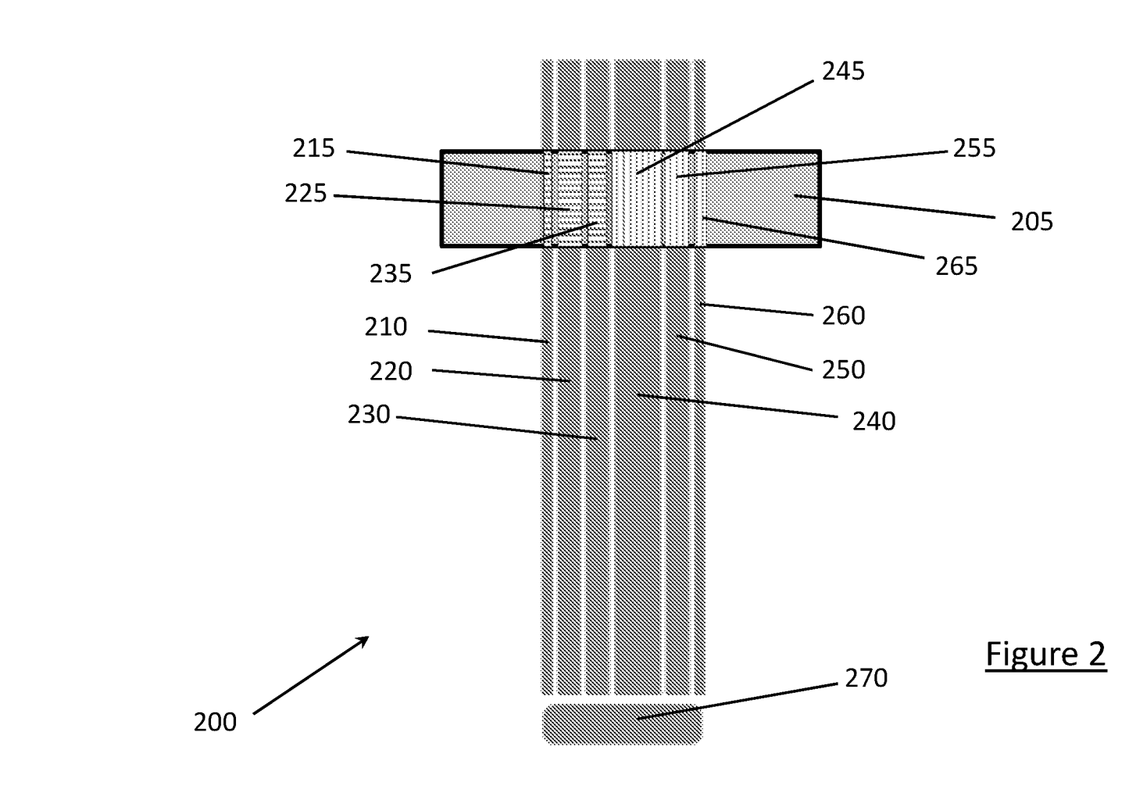
FIG. 2 is a schematic view of another embodiment of an electrochemical test strip that may be used with the described embodiments.

FIG. 2 shows an alternative test strip design that may be used. Whilst test strip 200 is similar in design to test strip 100, in FIG. 2 a limited number of features are shown for clarity and simplicity. It should be understood that elements of test strip 100 may readily be used with test strip 200 without departing from the scope of the contemplated embodiments.

Test strip 200 comprises from left to right fill detect electrode 210, working electrode 220, counter/reference electrode 230, counter/reference electrode 240, working electrode 250, and fill detect electrode 260. Working electrodes 220 and 250 are analyte sensing electrodes, and may be sensitive to the same analyte or may detect up to two different analytes in a single fluid sample applied to test strip 200. Test trip 200 also comprises a trigger bar 270, similar to meter switch-on bar 113 in FIG. 1.

Shown schematically is a sample-receiving chamber 205 disposed perpendicularly to electrodes 210-260. Chamber 205 may be similar in design and function to chamber 170 of test strip 100. A volume defined by chamber is bounded by portions 215, 225, 235, 245, 255, and 265 of respective electrodes 210-260. Thus, portions 215, 225, 235, 245, 255, and 265 are exposed to the interior of chamber 205 such that a fluid sample flowing through chamber 205 may flow into contact with each of portions 215-265. In much the same way as test strip 100 of FIG. 1, a first reagent layer (shown with horizontal hatching) coats portions 215-235 and a second reagent layer (shown with vertical hatching) coats portions 245-265. First reagent layer and second reagent layers have the same concentration of reagent, although in other embodiments the concentrations may be different.

A width of counter/reference electrode 240 is greater than that of working electrode 250 and in particular is twice the width of working electrode 250 within chamber 205. Thus, when blood or another fluid sample flows through chamber 205, it will flow into contact with twice as much reagent coating portion 245 than it does reagent coating portion 255. In other embodiments, the widths of other electrodes may be varied such that they may differ from one electrode to another electrode.

Figure 3:
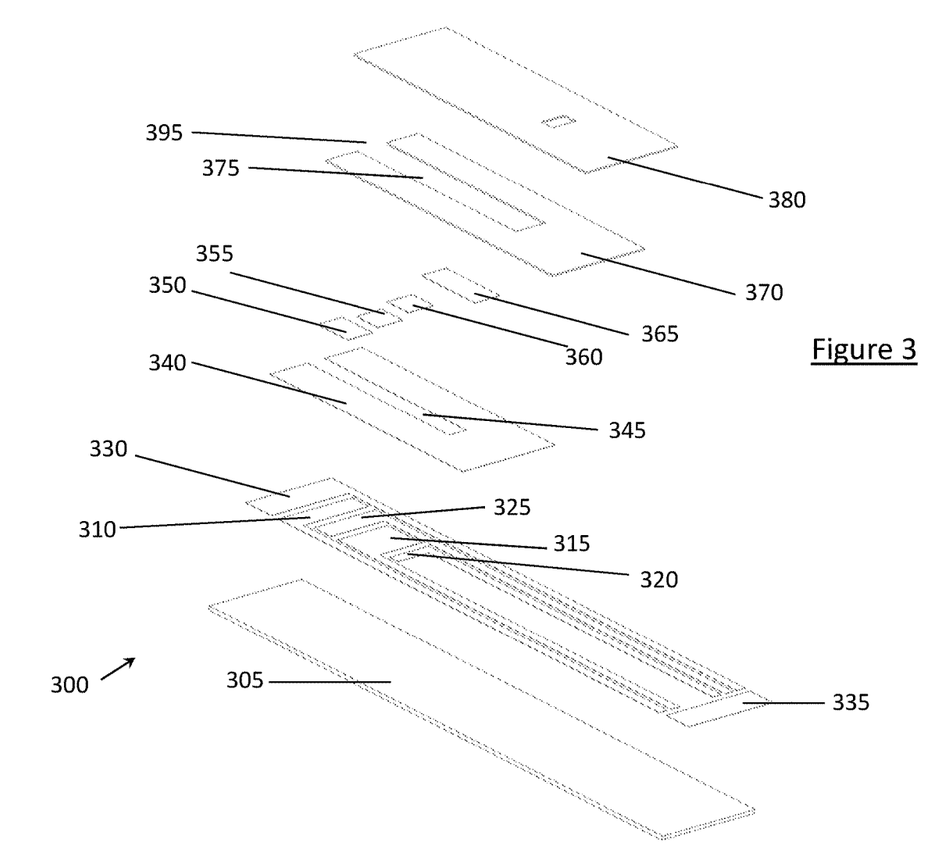
FIG. 3 is an exploded view of another embodiment of an electrochemical test strip that may be used with the described embodiments.

FIG. 3 shows a third embodiment of a test strip that may be used, this time for an end-fill strip (in contrast to the test strips of FIGS. 1 and 2 which as explained above are known as a side-fill strips in that a fluid sample is introduced at either side of test strip 100). Again, for simplification and clarity only certain elements of test strip 300 are shown, although it should be understood that elements of test strip 100 or 200 may readily be used with test strip 300 without departing from the scope of the contemplated embodiments.

From bottom to top, test strip 300 comprises a first substrate layer 305. A number of carbon electrodes 310-330 are provided, in much the same way as in the test strips of FIGS. 1 and 2. Other materials may be used for the electrodes, such as gold, carbon, graphene, platinum, palladium, gold/palladium composites, indium tin oxide film, or platinised carbon. From left to right, the electrodes are: first working electrode 310, second counter/reference electrode 315, fill detect electrode 320, second working electrode 325, and first counter/reference electrode 330.

A meter switch-on bar 335 is provided at the base of the electrode tracks. A dielectric layer 340 is then deposited on top of electrodes 310-330. Dielectric layer 340 comprises a channel 345 formed within to expose portions of electrodes 310-330. Reagent layers 350-365 are then deposited such that reagent layer 350 coats first counter/reference electrode 330, reagent layer 355 coats first working electrode 310, reagent layer 360 coats second working electrode 325, and reagent layer 365 coats second counter/reference electrode 315 and fill detect electrode 320. A spacer layer 370 comprising a channel 375 is then deposited on reagent layers 350-365. A top cover or second substrate layer 380 is then positioned over spacer layer 370. Spacer layer 370 together with channel 375 allows a chamber to be formed, the chamber (seen in more detail in FIG. 4) adapted to receive a fluid sample. The chamber defines a volume bounded by spacer layer 370, portions of reagent layers 350-365, and second substrate layer 380.

Similarly to electrodes 240 and 250 in test strip 200, second counter/reference electrode 315 is shaped such that, as compared to second working electrode 325, a greater portion of electrode 315 is within the chamber, or in other words bounds the volume of the chamber. Thus, as compared to reagent in reagent layer 360, a greater amount of reagent in reagent layer 365 is located within the chamber. Therefore, when a fluid sample is applied to end-fill strip via aperture 395, a greater amount of reagent in reagent layer 365 than reagent in reagent layer 360 will electrochemically react with the sample. The proportion of reagent in reagent layer 365 to reagent in reagent layer 360 is in accordance with a predetermined relationship, and in this case is a ratio of approximately 2:1. The ratio of the amount of reagent in reagent layer 350 within the chamber to the amount of reagent in reagent layer 355 within the chamber is 1.5:1.

Figure 4:
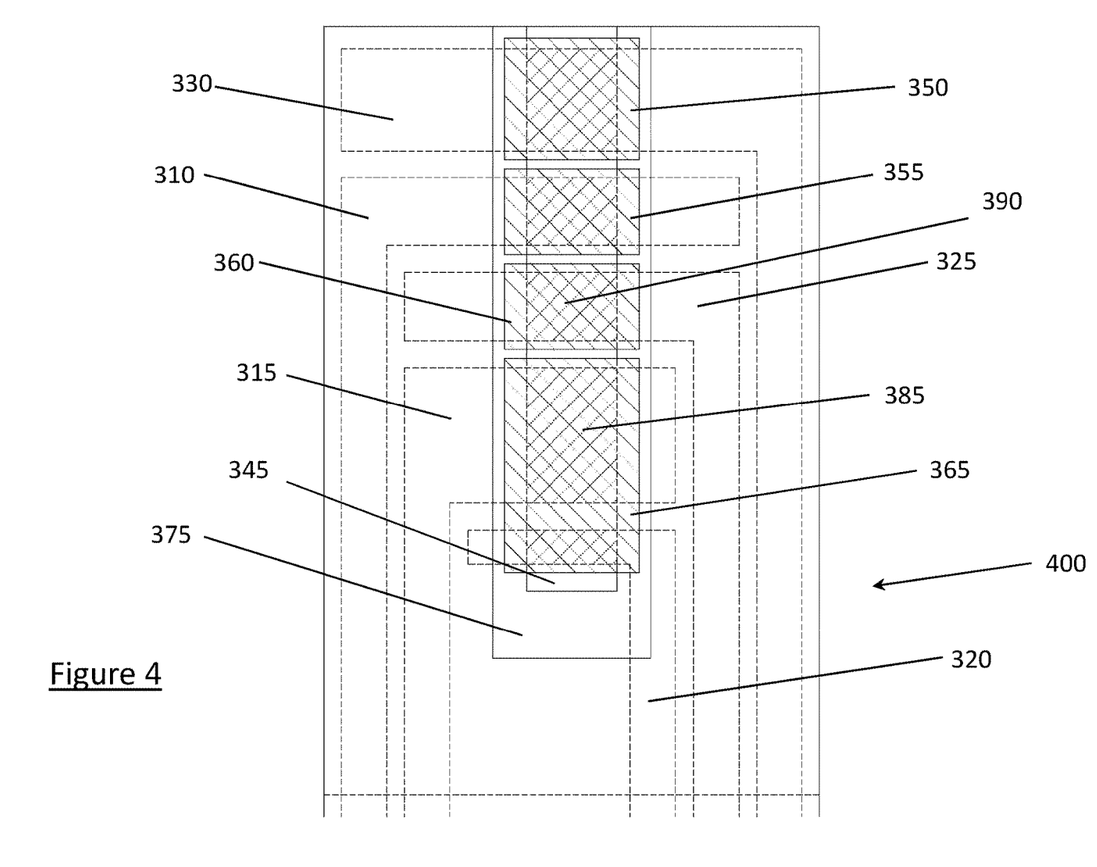
FIG. 4 is a schematic view of the electrochemical test strip of FIG. 3.

FIG. 4 shows a top-down view of reagent layers 350-365 coating portions of electrodes 310-330 within the chamber (second substrate layer 380 has been omitted from FIG. 4 for clarity). The portions of electrodes 310-330 comprising crossed hatching represent portions of electrodes coated in reagent and within the chamber, e.g. bounding the volume defined by the chamber. As can be seen, portion 385 of second counter/reference electrode 315 comprises approximately twice as much reagent in reagent layer 365 as portion 390 of second working electrode 325 comprises reagent in reagent layer 360.

Figure 5:
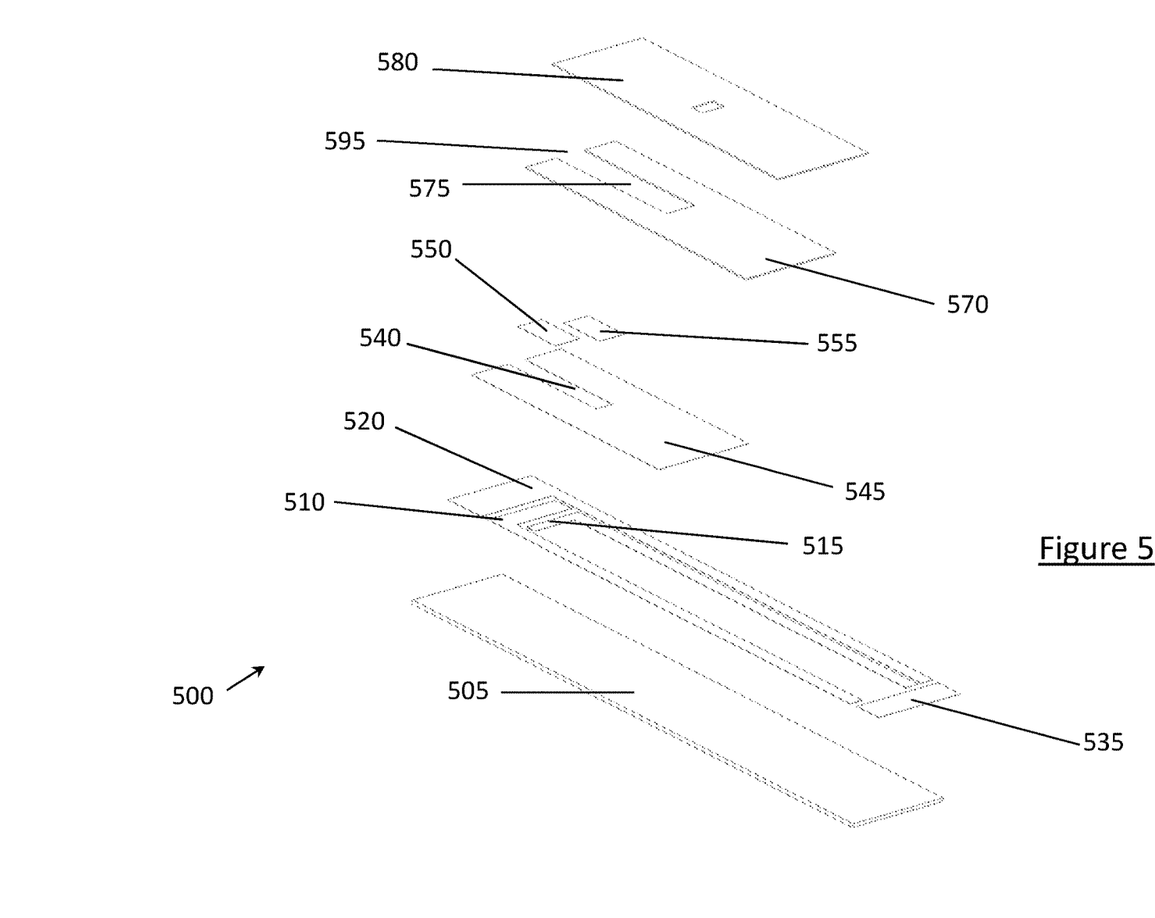
FIG. 5 is an exploded view of another embodiment of an electrochemical test strip that may be used with the described embodiments.

FIG. 5 shows an alternative embodiment of a test strip 500 in accordance with the present invention. Test strip 500 is similar to test strip 400 except that a pair of working—counter/reference electrode has been removed, leaving working electrode 510 and counter/reference electrode 520. Elements of test strip 500 are labelled according to like features of test strip 300. For example, the test strip 500 includes a spacer 570, a channel 575, a dielectric layer 545 comprising a channel 540, a meter switch on bar 535, and a first substrate layer 505.

Figure 6:
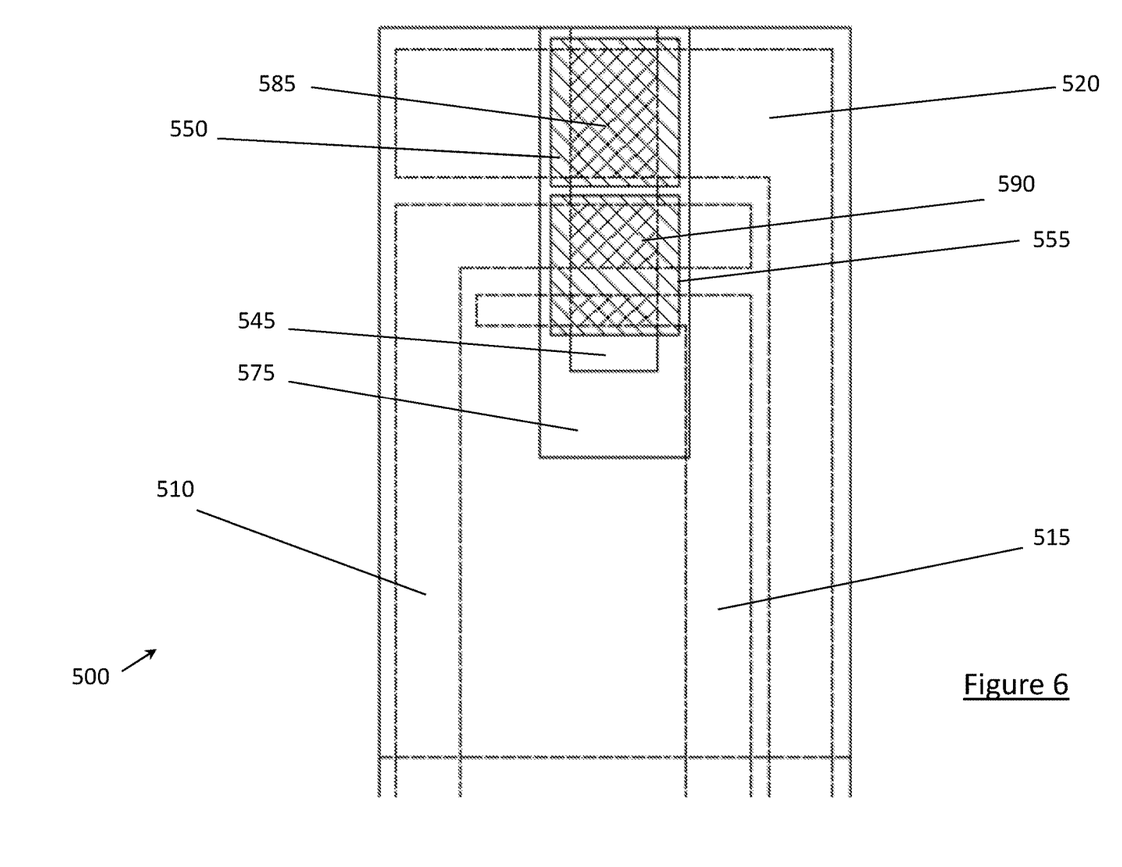
FIG. 6 is a schematic view of the electrochemical test strip of FIG. 5.

FIG. 6 shows a top-down view of reagent layers 550 and 555 coating portions of electrodes 510, 515, 520 within the chamber (second substrate layer 580 has been omitted from FIG. 6 for clarity). The portions of electrodes 510, 515, 520 comprising crossed hatching represent portions of electrodes coated in reagent and within the chamber, e.g. bounding the volume defined by the chamber. As can be seen, portion 585 of counter/reference electrode 520 comprises approximately twice as much reagent in reagent layer 550 as portion 590 of working electrode 510 comprises reagent in reagent layer 555.

Figure 7:
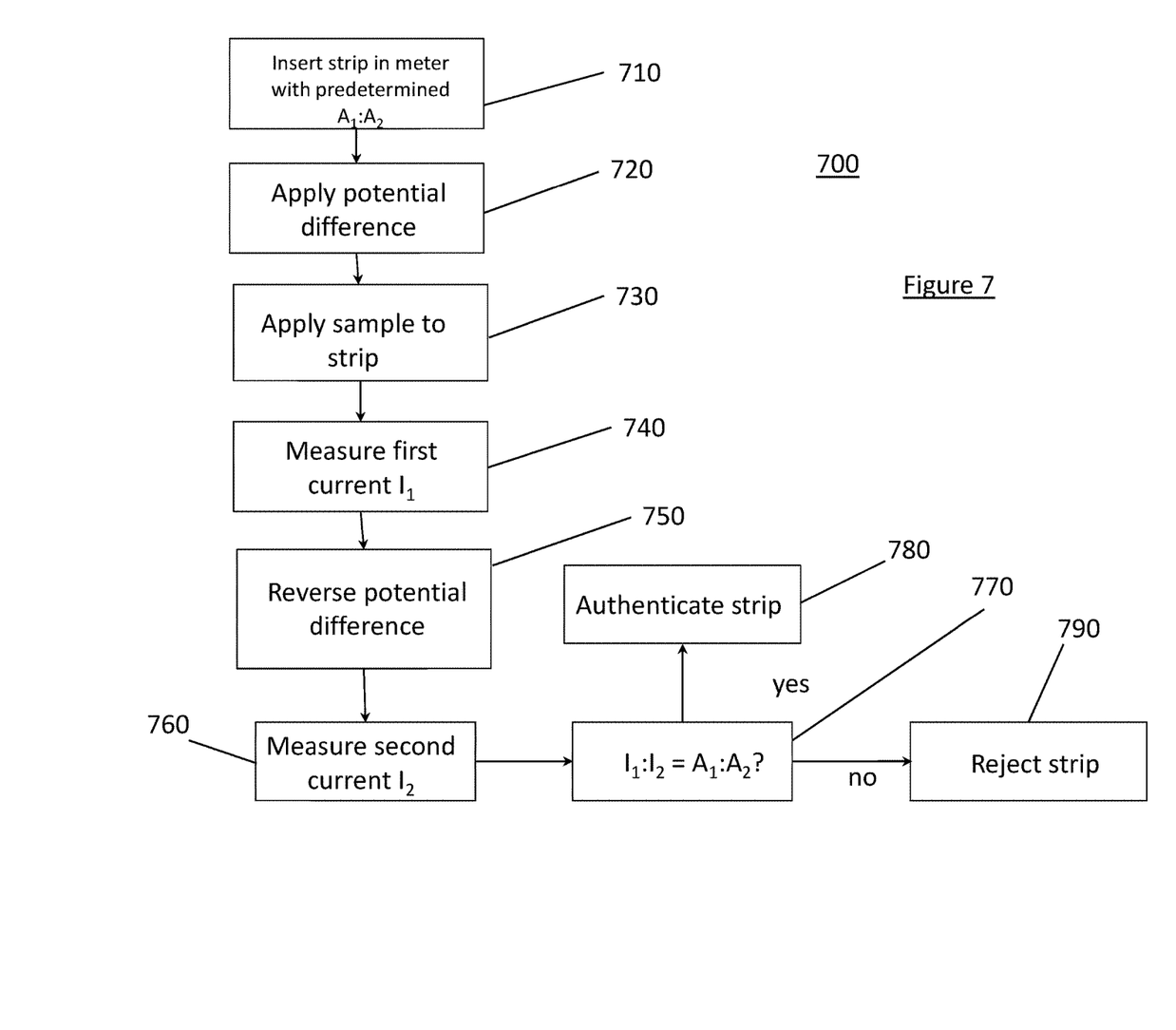
FIG. 7 is a flowchart showing the steps taken by a method in accordance with an embodiment.

Now turning to FIG. 7, there is shown method of authenticating a test strip, in accordance with an embodiment. The method is described in connection with the embodiment of FIGS. 5 and 6, but other strips such as those of FIGS. 1, 2, 3 and 4 may be used.

It should be noted that FIG. 7 shows an example method 700, and the order of the steps may be changed (for example the point in time at which the strip is inserted in the meter) without departing from the scope of the contemplated embodiments. The method may also comprise a fewer or greater number of steps.

At step 710, test strip 500 of FIGS. 5 and 6 is inserted into a meter in a reading position. In the reading position, working electrode 510 is connected to a voltage source whilst counter/reference electrode 520 is connected to ground. The portions 585 and 590 of working electrode 510 and counter/reference electrode 520 within the chamber of strip 500 have a predetermined area ratio $A_1:A_2$ (in this case 2:1). At step 720, a potential difference (e.g. 400 mV) is applied across working electrode 510 and counter/reference electrode 520. At step 730, a blood sample is applied to strip 500 by applying the blood sample at aperture 595. In some embodiments, it may be possible to apply the blood sample to the strip before the strip is received in the meter, depending on the strip and/or meter architecture.

The blood flows from counter/reference electrode 520 to working electrode 510, moving into contact with portions of reagent layers 550 and 555. Particular analyte or analytes in the blood sample electrochemically react with reagent layers 550 and 555, depending on the fluid sample and reagent used. Because reagent layer 555 is present on counter/reference electrode 520, the same biochemical conversion of analyte to product, with the formation of reduced mediator, takes place at counter/reference electrode 520 (the counter reaction will balance the working reaction in terms of charge consumed). The amount of reduced mediator depends upon the reaction taking place at working electrode 510. At step 740, a measurement of a first current $I_1$ generated at electrodes 520 and 510 is taken.

At step 750, the applied voltage is reversed such that a positive voltage is applied at counter/reference electrode 520. This time, an oxidative reaction takes place at counter/reference electrode 520 which is balanced by the reduction occurring at working electrode 510. At step 760, a measurement of a second current $I_2$ generated at electrodes 520 and 510 is taken. Because of the difference in area of portions 585 and 590 within the sample-receiving chamber, $I_2$ will be different to $I_1$.

At step 770, the meter compares the ratio of $I_2$ to $I_1$ with the ratio of $A_2$ to $A_1$. If the ratios are equal (or at least within a predetermined range) then at step 780 the meter authenticates strip 500 and for example may use the current measurements it has taken to determine the quantity of analyte(s) in the fluid sample. If not, then at step 790 the meter rejects strip 500 and for example may display an error message to the user. The user would have to use another strip to effect new measurements.

This can be shown experimentally (for example using the test strip of FIGS. 5 and 6) by scanning the applied voltage from negative to positive values. During the negative phase, e.g. when working electrode 510 is polarised negatively with respect to counter/reference 520, a reduction takes place at working electrode 510 which is balanced by the reaction occurring at counter/reference electrode 520. During the positive phase, e.g. when working electrode 510 is polarised positively with respect to counter/reference 520, working electrode 510 acts as the anode and the reduction is balanced at counter/reference electrode 520. The magnitude of the currents measured is determined ultimately by the reagent-coated surface areas or respective portions 585 and 590 of counter/reference electrode 520 and working electrode 510 within the chamber. Different reagent-coated surface areas will produce different current measurements.

Figure 8:
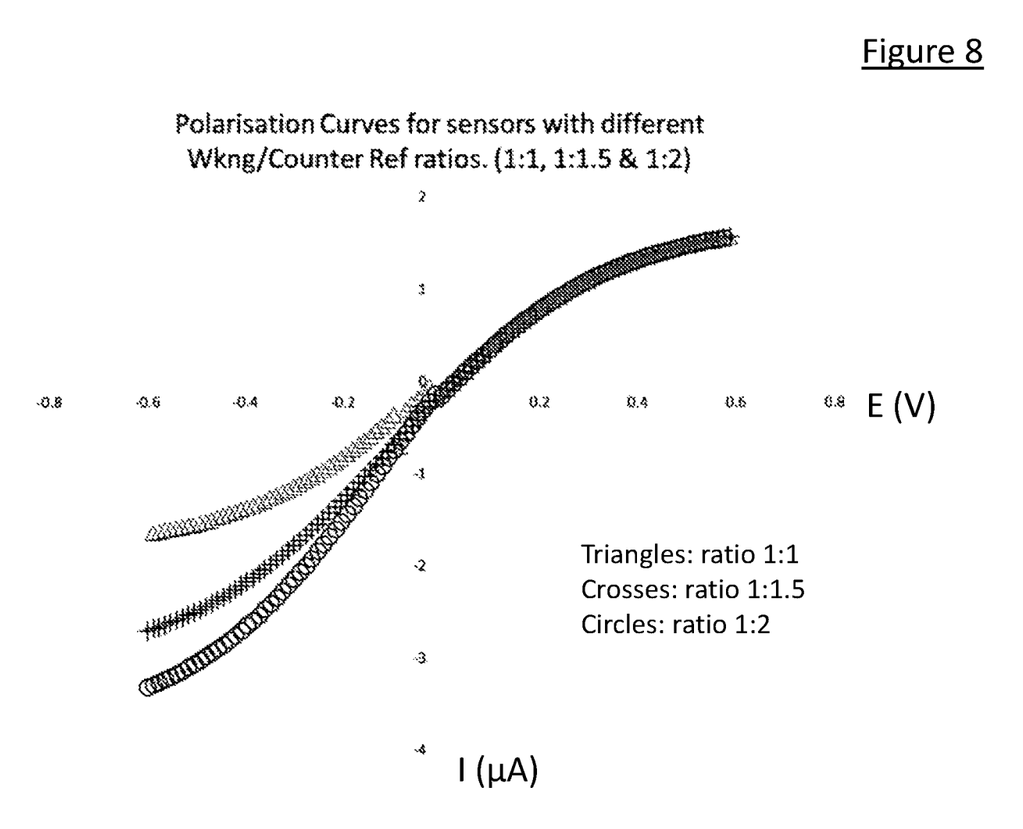
FIG. 8 is a graph showing different polarisation curves for different electrode area ratios.

FIG. 8 shows one such outcome from three different test strips. The reagent-coated area of the working electrode to the reagent-coated area of the counter/reference electrode is: 1:1 (open triangles); 1:1.5 (crosses); or 1:2 (open circles). The table below shows the absolute ratio of currents detected at +0.4 V and −0.4V for the above test strip designs.

| Electrode area ratio | Current at 0.4 V (mA) | Current at −0.4 V (mA) | Absolute current ratio |
|---|---|---|---|
| 1:1 | 1.31 | −1.37 | 1.05 |
| 1:1.5 | 1.35 | −2.08 | 1.54 |
| 1:2 | 1.31 | −2.65 | 2.02 |

The same principle would apply if portions 585 and 590 were of equal area but if different quantities of reagent coated portions 585 and 590 of electrodes 520 and 510 (for example if the method were applied using test strip 100 of FIG. 1). The different quantities of reagent may be a function of for example the concentration or surface area density of reagent coating portions 585 and 590 of counter/reference electrode 520 and working electrode 510.

Figure 9:
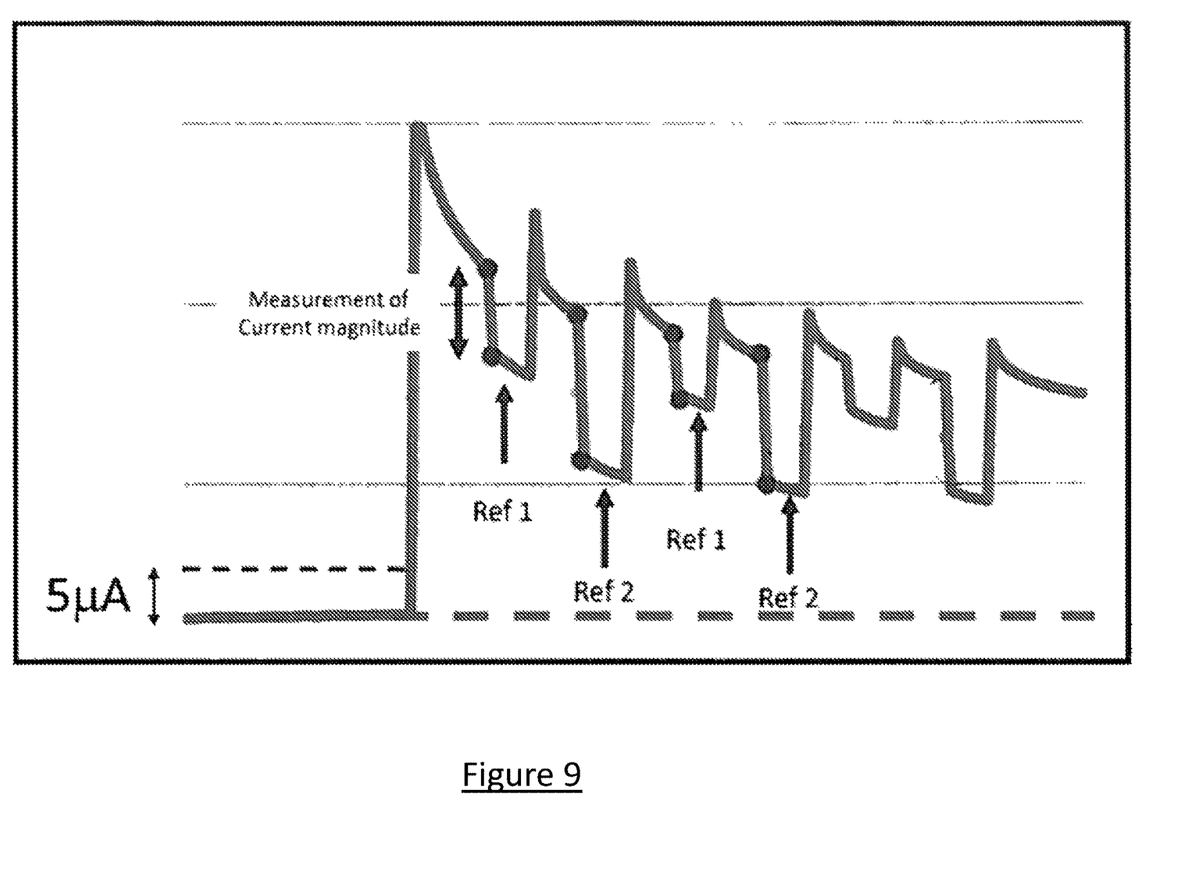
FIG. 9 is a graph showing measured current as a function of time, using the electrochemical test strip of FIG. 2.

In a separate experiment the test strip of FIGS. 3 and 4 was used. The same chemistry was deposited across the whole of the test strip. The current output from the test strip when counter/reference electrodes 315 and 330 were sequentially reversed in terms of applied potential (0.4V and −0.4V) was measured. The outcome can be seen in FIG. 9. As expected, during all of the potential reversal cycles the current generated from the counter/reference electrodes 315 and 330 was 1:2.

In another embodiment, two reference (non-measurement) electrodes may be manufactured on the same strip. The reference electrodes may have predefined differences in area such that respective portions of each reference electrode bounding the measurement chamber volume have a predetermined relationship or ratio. The magnitude of currents detectable from each reference electrode is proportional to the area of that electrode, and therefore the ratio of currents detected from both electrodes contains information on the ratio of the electrode areas. It is therefore possible, by manipulating the areas of the reference electrodes, to establish two or more ranges of current ratios which may allow a meter to determine which of two or more items of information are being conveyed (for example strip authentication). The practical limit to the number of such ranges will depend on the manufacturing variability in the areas of the electrodes, and other sources of measurement noise and uncertainty. Below is an outline of a means for using information on variability and misclassification risk to determine the practical sizes and number of current ranges.

In this regard we refer to D. V. Hinkley (1969), "*On the ratio of two correlated normal random variables*", *Biometrika*, 56(3), 635-639. If the ratio in question is $W=X_1/X_2$, then under certain assumptions regarding the measurements a reasonable approximation to the probability distribution function of W is:

$$F(w) = \Phi\left(\frac{\mu_2 w - \mu_1}{\sigma_1 \sigma_2 a(w)}\right), \ a(w) = \sqrt{\frac{w^2}{\sigma_1^2} + \frac{1}{\sigma_2^2}}$$

Figure 10:
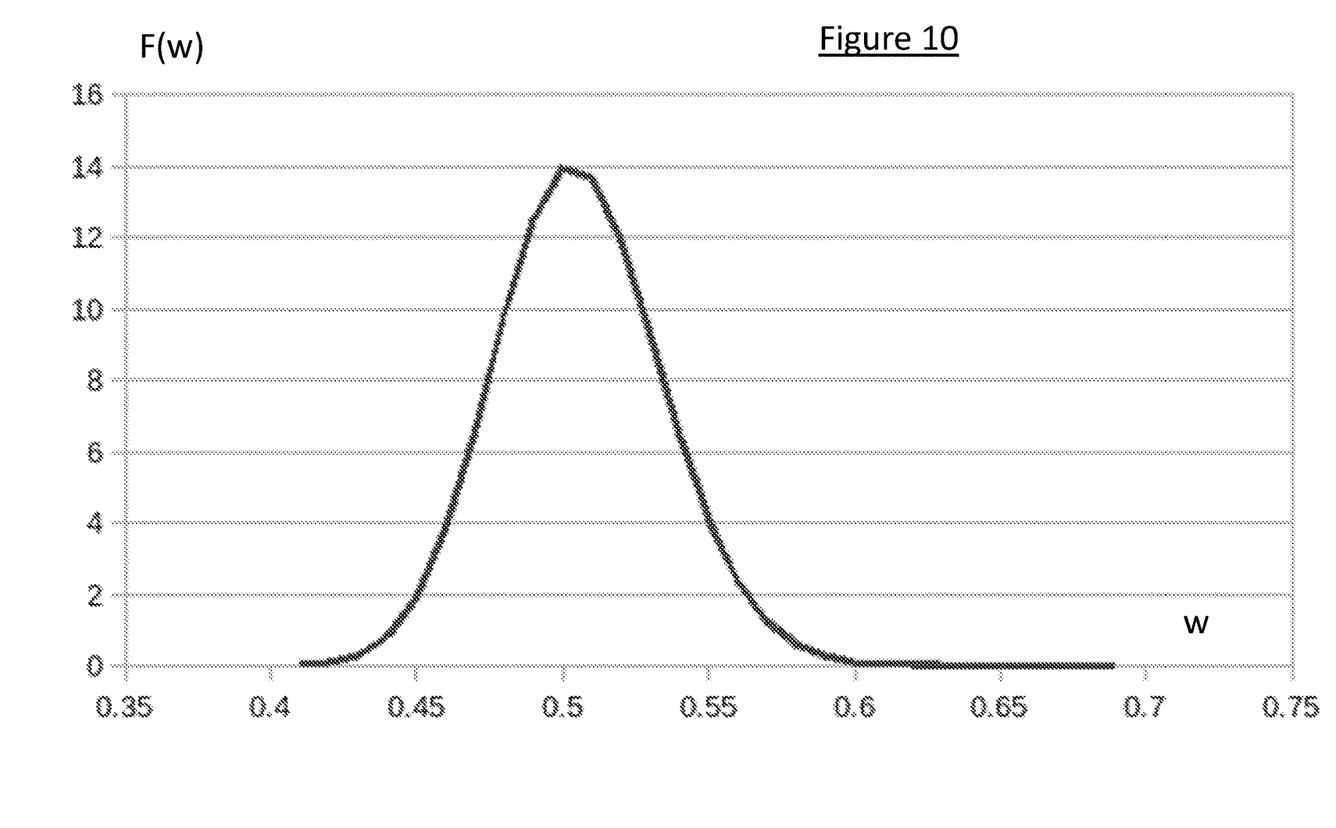
FIG. 10 is a graph showing the probability density function F(w).

Here, m denotes a mean, σ a standard deviation and F the standard normal distribution function. The means and standard deviations of two target currents are design inputs for ascertaining the distribution of their ratio. For example, if the means are 1.0 and 2.0, and the standard deviations are 0.04 and 0.08, then the resulting distribution function can be seen in FIG. 10. FIG. 10 shows the probability density function for the ratio in this example. The range of ratio values which would result in determining that ½ is the target would be set by how small the tails (error probability) need to be, and how many other target ranges are required.

Any feature of the above-described embodiments may be combined with the features of another embodiment, by making the appropriate changes. In addition, whilst described in connection with preferred embodiments, it is to be understood that the contemplated embodiments are not limited to those explicitly described, and that alterations, modifications, and variations of these embodiments may be carried out by the skilled person without departing from the scope of the claims. For instance, whilst described primarily in the context of authenticating electrochemical devices with a meter, it may equally well be used in other fields, for example in health and fitness, food, drink, bio-security applications, environmental sample monitoring, etc.

Furthermore, whilst primarily described in the context of its use with electrochemical test strips, the contemplated embodiments may extend to other electrochemical devices, such as wearable devices that actively acquire a fluid sample (such as interstitial fluid) from a user and cause an electrochemical reaction to occur with the sample. Examples of such are continuous (or semi-continuous) glucose monitoring devices used for controlling glucose concentrations (and insulin dosing) by users with diabetes.

The invention claimed is:

1. A method of using an electrochemical device comprising:
   at least first and second electrodes;
   a chamber for receiving a fluid sample and defining a volume partially bounded by a first portion of the first electrode and a second portion of the second electrode, the first portion having a first characteristic for influencing an electrochemical reaction at the first portion, the second portion having a second characteristic for influencing an electrochemical reaction at the second portion, the first and second characteristics having a predetermined relationship, and wherein the method comprises:
   receiving the fluid sample in the chamber;
   measuring first and second electrical outputs across at least one of the first and second electrodes; and
   determining whether the first and second electrical outputs are related according to the predetermined relationship;
   wherein measuring the first and second electrical outputs comprises:
      applying a first potential difference across the first electrode and the second electrode;
      measuring the first electrical output;
      applying a second potential difference across the first electrode and the second electrode; and
      measuring the second electrical output.

2. The method of claim 1, wherein one of the first and second electrodes is a working electrode.

3. The method of claim 1, wherein one of the first and second electrodes is: a counter electrode; or a counter and a reference electrode.

4. The method of claim 1, wherein at least one of the first and second portions comprises a sensing chemistry for electrochemically reacting with a fluid sample.

5. The method of claim 4, wherein the sensing chemistry comprises at least one of a mediator and a reagent.

6. The method of claim 1, wherein at least one of the first and second portions is partially or fully coated with a sensing chemistry for electrochemically reacting with a fluid sample.

7. The method of claim 1, wherein the first characteristic comprises a first area of the first portion of the first electrode and wherein the second characteristic comprises a second area of the second portion of the second electrode and wherein the predetermined relationship comprises a ratio of the first area to the second area.

8. The method of claim 7, wherein at least one of the first area and the second area comprises an area coated with a sensing chemistry.

9. The method of claim 1, wherein the first characteristic is a quantity of sensing chemistry comprised in the first portion, and wherein the second characteristic is a quantity of sensing chemistry comprised in the second portion and wherein the predetermined relationship comprises a ratio of the quantity of the first sensing chemistry to the quantity of the second sensing chemistry.

10. The method of claim 1, wherein the first characteristic is a first concentration of a sensing chemistry coating the first portion, and wherein the second characteristic is a second concentration of a sensing chemistry coating the second portion.

11. The method of claim 10, wherein at least one of the first and second concentrations comprises a surface area density or a volume density.

12. The method of claim 10, wherein the predetermined relationship comprises a ratio of the first concentration to the second concentration.

13. The method of claim 1, wherein the second potential difference is a reverse of the first potential difference.

14. The method of claim 1, wherein the first and second electrical outputs comprise respective first and second currents generated through the first electrode and the second electrode.

15. The method of claim 1, wherein the electrochemical device is an electrochemical test strip or a wearable electrochemical device.

16. The method of claim 1, further comprising authenticating the electrochemical device if the first and second electrical outputs are related according to the predetermined relationship.

17. The method of claim 1, wherein the fluid sample comprises:
   a bodily fluid selected from the following: blood, plasma, urine, saliva, lacrimal fluid, sweat, and interstitial fluid; or
   breath condensate.

* * * * *